United States Patent [19]

Kay

[11] 4,311,740
[45] Jan. 19, 1982

[54] INDENTIFICATION STRIP ASSEMBLY AND METHOD OF USE THEREOF

[75] Inventor: Paul O. Kay, Barrington, Ill.

[73] Assignee: Hollister Incorporated, Chicago, Ill.

[21] Appl. No.: 159,363

[22] Filed: Jun. 13, 1980

[51] Int. Cl.³ .................. B05D 1/28; B65D 65/28; G09F 3/20; B65D 65/32

[52] U.S. Cl. .................... 427/428; 428/43; 40/10 D; 40/19; 40/21 C; 282/27.5; 282/2; 282/8 A; 282/22 R; 427/275

[58] Field of Search ............. 40/19, 21 C, 10 D, 2 R; 428/43, 77, 914; 282/27.5, 2, 8 R, 8 A, 22 R, DIG. 2; 427/275, 428, 256

[56] References Cited

U.S. PATENT DOCUMENTS

| | | | |
|---|---|---|---|
| 2,954,620 | 10/1960 | Schneider | 40/21 C |
| 3,027,665 | 4/1962 | St. John | 40/21 C |
| 3,889,411 | 6/1975 | Laugherty | 40/21 C |
| 4,093,277 | 6/1978 | Nolan et al. | 282/24 R |

Primary Examiner—Marion McCamish
Assistant Examiner—Alexander S. Thomas
Attorney, Agent, or Firm—Tilton, Fallon, Lungmus

[57] ABSTRACT

An identification strip assembly especially adapted for use with tubular insert-receiving identification bands, such assembly taking the form of a base strip and an overlying cover strip. The base strip includes handle, insert, and tip sections delineated by transverse lines of perforation. The cover strip is secured only to the handle and tip sections of the base strip, is transversely perforated along a line disposed above the boundary between the handle and insert sections of the base strip, and is provided with means for producing an image on the insert section when such section, and the portion of the cover strip above it, are subjected to compressive force. The perforation lines are formed to tear or break preferentially so that when a user grips the assembly to snap the tip and handle sections apart, two of the perforation lines will break simultaneously to disconnect the insert section from its cover and from the tip section while leaving the insert section still attached to the covered handle section. Following insertion of the insert section into a tubular identification band, the user may then snap the handle and insert sections apart to break the remaining perforation line.

16 Claims, 8 Drawing Figures

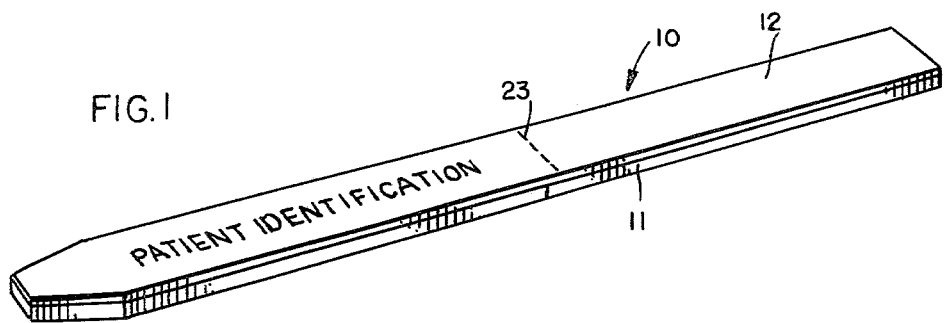
FIG. 1
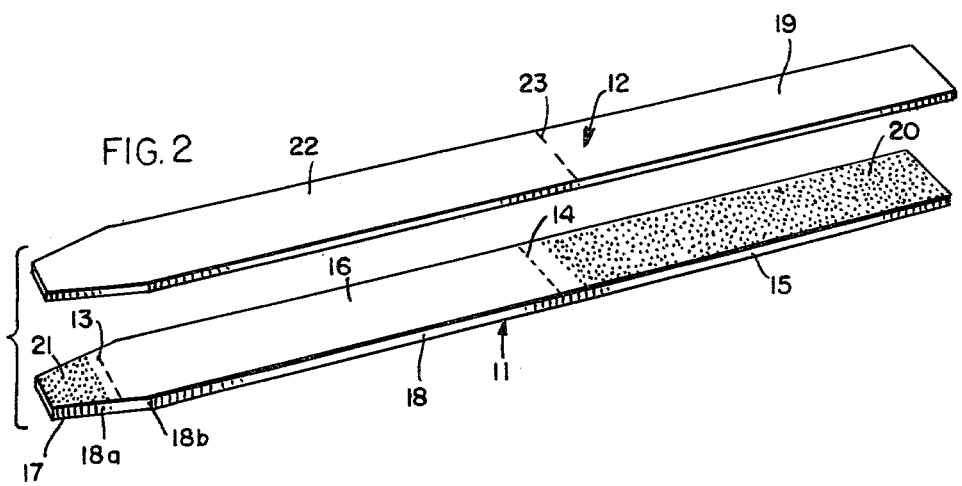
FIG. 2
FIG. 3
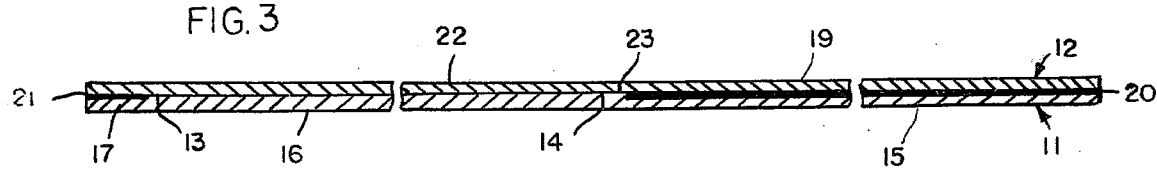
FIG. 4
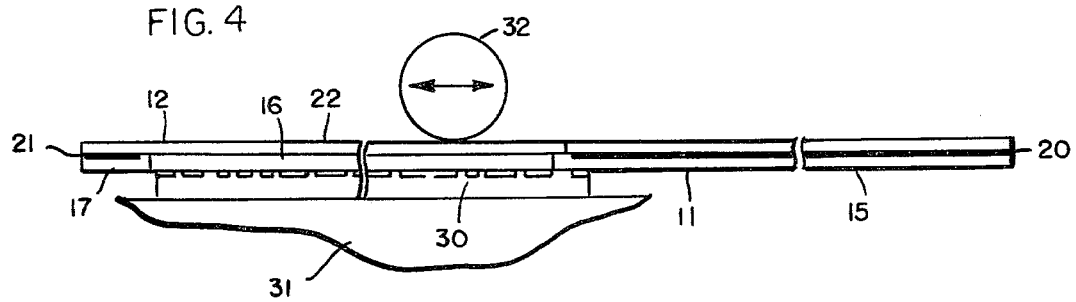

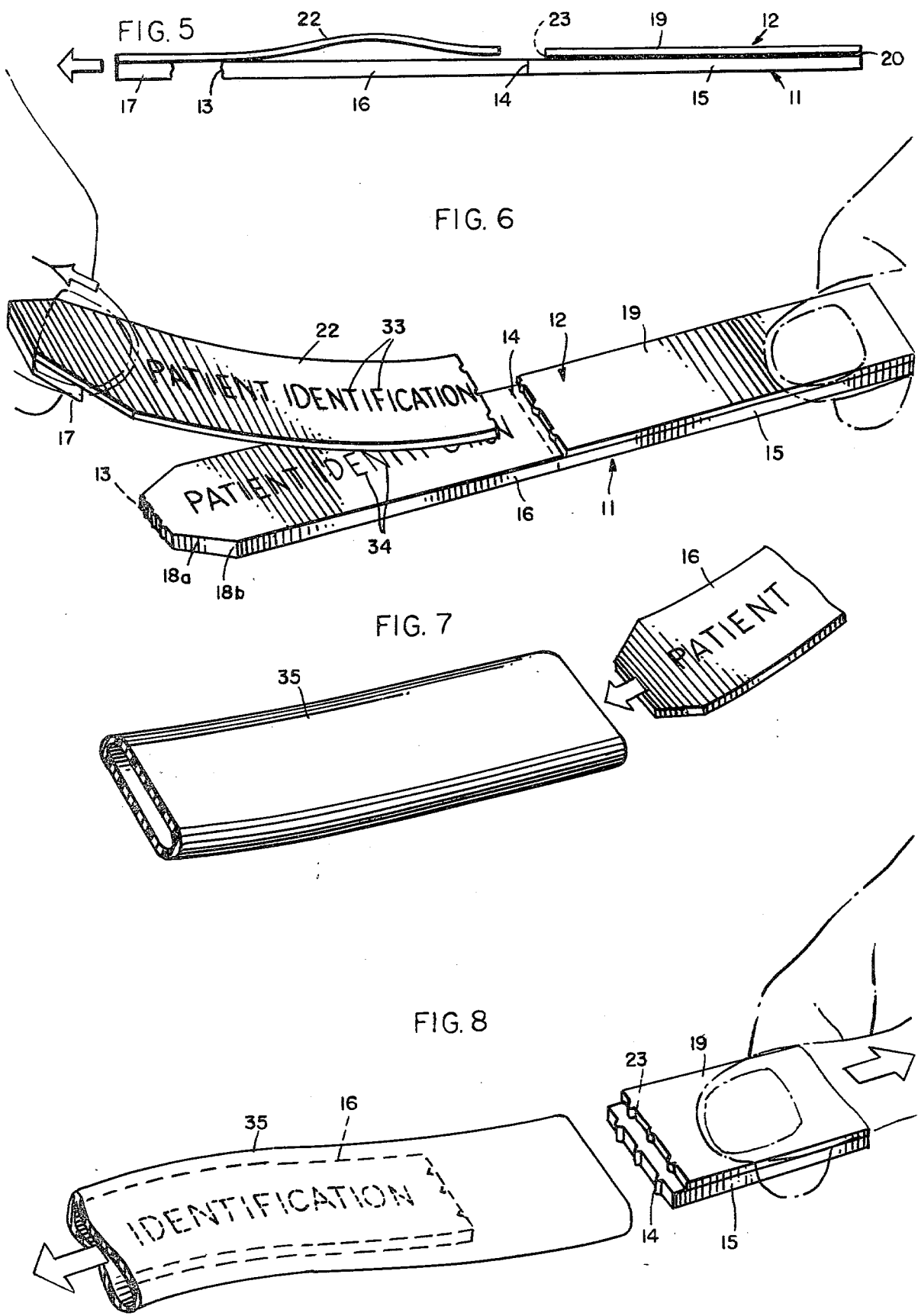

INDENTIFICATION STRIP ASSEMBLY AND METHOD OF USE THEREOF

BACKGROUND AND SUMMARY

U.S. Pat. No. 4,093,277 discloses a plurality of separable strips, each strip being divided into a handle section and an identification section. Carbon paper strips overlie the identification sections and are peeled away after patient identification has been imprinted on the identification section by a suitable imprinting device. The identification section of each strip is then inserted into a tubular bracelet, and the handle section is detached along a line of perforation.

Although the system so described is widely used, it does have certain disadvantages. For example, removal of the carbon paper following imprinting ordinarily may result in a tearing of that paper. An end portion of the carbon paper strip may remain adhesively attached to the base strip and, even if the residual portion is not actually coated with carbon or other image-transferring material, such residuum nevertheless mars the appearance of the completed band. While pressure-sensitive adhesives might be used to permit separation of the carbon paper from the base strip without tearing of the strip, consistency of operation is difficult to achieve because of changes occurring in such adhesives when subjected to different storage conditions and storage intervals. In fact, carbon paper of the type used in such a system has only a limited shelf life for approximately six to nine months; after that, it tends to harden and produce an increasingly faint image.

In modern hospital operations, an identification card or plate is ordinarily prepared for each patient at the time of admission, such card having raised indicia setting forth relevant information concerning the patient and, in general, having the appearance of a typical plastic credit card. Since the hospital normally uses such an identification card, in conjunction with a standard ink roller imprinter, to mark charts, reports, invoices, and most other documents pertaining to the patient, it would be advantageous to use such a card and imprinter for applying a patient's name and other identifying data to the insert strip for an identification bracelet. Although the system of U.S. Pat. No. 4,093,277 may be so used, the arrangement necessarily results in ink from the roller being applied to the outer surface of the carbon paper and, consequently, during subsequent peeling away of that carbon paper, a user may find it difficult to avoid getting either ink from the imprinter or carbon from the underside of the carbon paper onto his (her) fingers, clothing, and nearby objects.

Accordingly, it is a principal object of this invention to provide an improved identification strip assembly, and its method of use, in which a conventional ink roller imprinter may be utilized to imprint an insert strip and, after such imprinting, a protective cover may be easily and quickly removed from the insert strip, and the insert strip may be readily inserted into a tubular identification bracelet, followed by detachment of a handle section of the insert strip, all with greater facility and less likelihood of ink-finger contact than in the use of prior devices. Another object is to provide a device which may be easily and quickly used to produce a final bracelet assembly having an improved appearance when compared with the use of prior devices.

Briefly, the identification strip assembly comprises an elongated base strip having a tip section at one end, a handle section at the opposite end, and an insert section therebetween. Overlying the base strip is a cover strip, one portion of the cover strip being secured to the handle section, another portion being secured to the tip section, and an intermediate portion extending over the insert section without being directly attached thereto. The cover strip must be capable of producing an image on the insert portion of the base strip when localized pressure is applied to the two components; for that purpose, the cover strip, or both the cover strip and the underlying insert section of the base strip, may be coated with impact-sensitive microcapsules which release image-producing dyes when ruptured, all as well known in the art in connection with what is commonly termed "carbonless" paper. Alternatively, conventional carbon paper may be used, as well as any other pressure-sensitive material which will result in the transfer or development of an image on the insert section of the base strip when pressure is applied by a typewriter, imprinting roller, writing instrument, or some other pressure-applying device.

The insert section of the base strip is delineated from the tip section and the handle section by two lines of perforation. A third line of perforation traverses the cover strip. The perforations are formed so that the resistance to separation along the perforation line between the insert section and the handle section of the base strip is greater than the combined resistance to separation of the line of perforation adjacent the tip section and the line of perforation across the cover strip. Consequently, following an imprinting step, a user may simply grip the assembly with the fingers of one hand holding the covered tip section and those of the other hand gripping the covered handle section and then, with an endwise snapping action, simultaneously break the line of perforation across the cover strip as well as the line of perforation across the base strip adjacent the tip section, while leaving intact the line of perforation between the handle section and the insert section. Still holding the device by its handle, the user may then feed the indicia-bearing insert section into a tubular plastic bracelet and, gripping the insert section between the walls of the bracelet, the exposed handle section may be snapped outwardly to break the base strip along the remaining line of perforation.

Ideally, the edges of the insert section taper inwardly immediately adjacent the tip section. As a result, the line of perforation adjacent the tip section tends to be broken more easily than the longer line of perforation between the insert and handle sections. Of even greater importance is the fact that following detachment of the tip section, such taper of the insert section facilitates insertion of that section into the interior of a tubular bracelet. Such insertion is also facilitated by the stiffening effect on the handle section produced by the remaining portion of the cover strip secured thereto, and by the adhesive which bonds such elements together.

Other references illustrative of the state of the art are U.S. Pat. Nos. 3,027,665, 2,954,620, 3,889,411, 3,179,441, and 2,719,735.

DRAWINGS

FIG. 1 is a perspective view of a patient identification strip assembly embodying the present invention.

FIG. 2 is an exploded perspective view of the strip.

FIG. 3 is a longitudinal cross sectional view of the strip.

FIG. 4 is a longitudinal view showing a first step of imprinting the strip.

FIG. 5 depicts a subsequent step of breaking apart the composite strip.

FIG. 6 is a perspective view of the breakaway step, illustrating the patient-identifying indicia remaining on the insert section.

FIG. 7 is a perspective view showing the insert section being introduced into the transparent plastic tube of an identification bracelet.

FIG. 8 is a fragmentary perspective view showing the final step of separating and removing the handle portion of the device.

DETAILED DESCRIPTION

Referring to the drawings, numeral 10 generally designates a patient identification strip assembly comprising a lower base strip 11 and a superimposed cover strip 12. The base strip is provided with transversely extending first and second lines of perforation 13 and 14, respectively, the latter being disposed approximately midway along the length of the base strip. Perforation line 14 is disposed between elongated handle and insert sections 15 and 16, whereas perforation line 13 is disposed between the insert section 16 and tip section 17.

The longitudinal side edges 18 of the base strip are generally straight and parallel; however, as they approach tip section 17 such edges converge along 18a so that the width of tip section 17 is reduced. It will be noted that since the taper commences at points 18b along the sides of insert section 16, and since such points are spaced from perforation line 13, the length of perforation line 13, extending transversely of the strip assembly 10, is less than that of perforation line 14. In addition, the perforations of line 14 are shorter than those of line 13, with the result that the greater number of bridging connections of line 14, combined with the greater length of that line, makes line 14 more resistant to tearing than line 13.

Cover strip 12 is coextensive in outline with base strip 11 and, therefore, covers the handle, insert, and tip sections 15-17 of the base strip. One portion 19 of the cover is secured by an adhesive bonding layer 20 to the handle section 15. Another adhesive bonding layer 21 secures tip section 17 to the portion of the cover extending thereover. Both bonding layers terminate short of perforation lines 14 and 13, and the insert section 16 of the base strip, although disposed directly beneath portion 22, is otherwise unattached to the cover strip. A perforation line 23 extends across the cover strip, being disposed in the region direct above transverse perforation line 14 of the base strip.

Perforation line 23 is shown to have relatively long perforations, similar to those of line 13 and substantially longer than those of line 14. The precise dimensions of the perforations, and particularly the dimensions of the bridging portions between such perforations, may be varied considerably, depending on such factors as the relative thicknesses of the strips 11 and 12 and the tear strengths of the materials used to fabricate such strips; however, it is essential that the resistance of the base strip to tearing or breaking along perforation line 14, when subjected to pulling forces in opposite directions applied to opposite ends of the elongated strip assembly, be greater than the combined resistance to tearing or breaking along perforation lines 13 and 23. If a user grips the covered handle section 15 between the fingers of one hand, and the covered tip section 17 between the fingers of the other hand, and then snaps the ends of the strip assembly apart, preferential breaking or fracture should occur along lines 13 and 23, with perforation line 14 remaining intact, as depicted in FIG. 5.

The cover strip 12 is provided with some means for producing an image on the insert section 16 of the base strip 11 when localized pressure is applied to the insert section and the overlying portion of the cover strip. Preferably such means takes the form of microencapsulated dye components applied as coatings to the opposing surfaces of the insert section and cover strip, such coatings being well known and widely used for "carbonless" manifolds. Reference may be had to U.S. Pat. No. 3,981,532, and the references cited therein, for coatings applied to what are known as CB and CF papers. While each of the layers or strips would thus be coated with different microencapsulated components which, when combined by pressure sufficient to rupture such capsules produce a readable image, it is apparent that all of the colorable components may be coated upon (or included within) one of the sheets, preferably cover sheet 12, in accordance with the teachings of U.S. Pat. No. 3,901,986 and other similar references. Moreover, cover strip 12 may be formed, if desired, of conventional carbon paper or any other suitable sheet material having its underside coated with a material which will transfer to the top surface of insert section 16 when localized compressive forces are applied to the two strips. Such localized forces may be applied by means of a pen, pencil, stylus, typewriter or other writing instrument but, as already indicated, would most commonly be applied by a roller-equipped imprinter of the type commonly used in hospitals and elsewhere to transfer information represented by the raised symbols of a plastic (or metal) card.

Strips 11 and 12 would ordinarily be formed of paper or thin paperboard stock although suitable plastics, plastic-paper laminates, and other materials capable of carrying and transmitting pressure-sensitive recording media, and of being torn or broken apart along lines of weakness, may be used. Should thermoplastics or thermoplastic laminates be used, strips 11 and 12 might be heat sealed together, in which case bonding layers 20 and 21 schematically depicted in the drawings would constitute zones of fused plastic material. Also, while the lines of perforation referred to herein would normally consist of a plurality of spaced slits or indentations, considerable variation in accordance with the teachings of the art would be possible for the purpose of achieving clean break-apart lines for whatever particular sheet material or materials are selected.

FIGS. 4-8 depict successive steps of using the strip assembly of the present invention. In FIG. 4, a conventional identification card 30 is supported upon a platen 31, and the raised symbols of that card are impressed into the underside of insert section 16 by means of a roller 32. Elements 31 and 32 schematically represent the platen and roller of a conventional roller imprinter. In the operation of such an imprinter, ink is normally applied by roller 32. Consequently, ink would normally be applied to the top surface of cover portion 22 to produce indicia 33 thereon corresponding to the raised symbols on card or plate 30 (FIG. 6). As is often the case, ink may also be applied by roller 32 to surrounding areas of the top surface of portion 22 and, in that connection, it is to be noted that cover portion 22 therefore performs a protective function by preventing ink from being applied by roller 32 directly to the underlying insert portion 16 of base strip 11. The indicia 34 formed on the top surface of insert section 16 is produced solely by the effect of localized pressure on the coating or coatings on one or both of the opposing surfaces of insert section 16 and the removable portion 22 of cover strip 12.

Following the imprinting step, the user simply grasps the covered tip portion 17 and handle portion 15 and snaps them apart in opposite directions to rupture perforation lines 13 and 23 in the manner depicted in FIG. 5. Cover portion 22, with tip section 17 still adhesively attached thereto, is withdrawn (FIG. 6) and may either be discarded or used for some other patient identification purpose. The tapered free end of insert section 16 is then introduced into the open end of a conventional tubular plastic identification bracelet (FIG. 7). Such a bracelet is well known and shown more fully in co-owned U.S. Pat. No. 3,027,665. After the insert section has been fully inserted into the tube or sleeve 35, the user squeezes the flexible walls of the tube to clamp the insert section therebetween and, with the other hand, snaps the covered handle section 15 outwardly to tear or break the base strip along the last remaining perforation line 14 (FIG. 8). The handle section 15, and the cover portion 19 adhesively secured thereto, may be discarded, having served the purposes of providing a gripping means for inserting the strip assembly into a suitable imprinter, then simultaneously tearing the assembly along perforation lines 13 and 23, then introducing the insert section to a bracelet tube, and finally breaking apart the base strip along perforation line 14.

The taper of the insert section defined by those portions of edges 18a extending from points 18b to perforation line 13 performs an important function in facilitating the insertion of the section 16 into a bracelet tube 35. Such taper performs a piloting function in directing or guiding the insert section into the tube.

The double thickness of handle section 15 and its cover portion 19, as well as the adhesive bonding interposed therebetween, tend to produce a stiffening effect which contributes to effective use of the handle, particularly during the step of introducing the insert section 16 of the base strip into the tube of the bracelet.

While in the foregoing I have disclosed an embodiment of the invention in considerable detail for purposes of illustration, it will be understood by those skilled in the art that many of these details may be varied without departing from the spirit and scope of the invention.

I claim:

1. A method of preparing an identification bracelet utilizing an identification strip assembly and a tubular transparent band adapted to be secured about the limb of a wearer; said strip assembly including a base strip having tip, insert, and handle sections, and also including a cover strip overlying said base strip; said cover strip being secured to said tip and handle sections and being provided with means for producing an image on said insert section when said insert section and cover strip are subjected to localized pressure; said base strip having a first perforation line between said tip and insert sections and a second perforation line between said insert and handle sections, and said cover strip having a perforation line overlying said second perforation line of said base strip; said second perforation line having greater tear resistance than the combined tear resistances of said first perforation line of said base strip and said perforation line of said cover strip; wherein the steps comprise applying pressure to said insert section and the portion of said cover strip overlying the same to produce an identifying image on said insert section; then abruptly urging apart said tip section and said handle section, along with the respective portions of said cover strip overlying the same, in opposite endwise directions to simultaneously tear said first perforation line of said base strip and said perforation line of said cover strip without tearing said second perforation line of said base strip; then inserting said insert section into a flexible transparent tubular band; and then tearing said second perforation line to separate said handle section and the portion of said cover strip overlying the same from said band while retaining said insert section within said band.

2. The method of claim 1 in which the end of said insert section adjacent to said first perforation line is tapered; said insert step involving inserting said tapered end of said insert section into said tubular band.

3. The method of claim 1 in which said compressive force is applied by an inked roller engaging the portion of said cover strip overlying said insert section, said cover strip protecting said insert section from contact by ink from said roller.

4. An identification strip assembly for use with tubular insert-receiving identification bands, comprising an elongated base strip of imprintable sheet material having a tip section at one end thereof, a handle section at the opposite end thereof, and an insert section disposed therebetween; said sections being delimited by a first perforation line extending transversely between said tip section and said insert section and a second perforation line extending transversely between said insert section and said handle section; and a cover strip overlying said sections and being secured to said tip and handle sections while being unsecured to said insert section; said cover strip having a transverse perforation line adjacent said second perforation line of said base strip; said second perforation line having greater tear resistance than the combined tear resistance of said first perforation line of said base strip and said perforation line of said cover strip; whereby, a user gripping said covered tip section and said covered handle section and then urging the same apart in opposite endwise directions may separate said tip section from said insert section along said first perforation line, and simultaneously separate said cover section along the perforation line thereof, without tearing said base strip along said second perforation line; said cover strip being provided with means for producing an image on said insert section when said insert section and the portion of said cover strip overlying the same are subjected to pressure.

5. The assembly of claim 4 in which said second perforation line extends across said base strip at about the longitudinal midpoint thereof.

6. The assembly of claim 5 in which said tip section is relatively short in relation to the length of each of said handle and insert sections.

7. The assembly of claim 4 in which said cover strip is coextensive in outline with said base strip.

8. The assembly of claim 1 in which said cover strip is adhesively secured to said tip and handle sections.

9. The assembly of claim 8 in which adhesive layers are disposed between said tip section and said cover strip, and between said handle section and said cover strip, for adhesively securing said strips together; said adhesive layers terminating short of said first and second lines of perforation.

10. The assembly of claim 9 in which said adhesive layer interposed between said handle section and said cover strip extends substantially the full length of said handle section.

11. The assembly of claim 4 in which said base strip has inwardly tapering side edges at said one end thereof.

12. The assembly of claim 11 in which said inwardly tapering side edges commence at points along said insert section spaced from said first perforation line and extend towards said one end to at least said first perforation line.

13. The assembly of claim 12 in which said first perforation line is shorter than said second perforation line.

14. The assembly of claim 12 in which said tapered side edges continue from said insert section along said tip section.

15. The assembly of claim 4 in which said means for producing an image on said insert section comprises microencapsulated dye components coating the opposing surfaces of said insert section and said cover strip.

16. The assembly of claim 4 in which said means for producing an image on said insert section comprises an opaque transferable coating along the underside of said cover strip overlying said insert section.

* * * * *